United States Patent
Tenckhoff et al.

(10) Patent No.: US 10,228,349 B2
(45) Date of Patent: Mar. 12, 2019

(54) NEUTRALIZATION OF CHARGED LUBRICANT

(71) Applicants: ZF Friedrichshafen AG, Friedrichshafen (DE); ZF WIND POWER ANTWERPEN N.V., Lommel (BE)

(72) Inventors: Georg Tenckhoff, Friedrichshafen (DE); Kurt Engelen, Mol (BE); Alejandro Martin Barrios, Lommel (BE)

(73) Assignees: ZF Friedrichshafen AG, Friedrichshafen (DE); ZF Wind Power Antwerpen N.V., Lommel (BE)

(*) Notice: Subject to any disclaimer, the term of this patent is extended or adjusted under 35 U.S.C. 154(b) by 0 days.

(21) Appl. No.: 15/632,440

(22) Filed: Jun. 26, 2017

(65) Prior Publication Data
US 2017/0370881 A1    Dec. 28, 2017

(30) Foreign Application Priority Data
Jun. 28, 2016   (DE) .................. 10 2016 211 615

(51) Int. Cl.
*G01N 27/60*   (2006.01)
*G01N 33/28*   (2006.01)
(Continued)

(52) U.S. Cl.
CPC ............. *G01N 27/60* (2013.01); *F16C 19/52* (2013.01); *F16C 41/00* (2013.01); *G01N 33/28* (2013.01); *G01N 33/2888* (2013.01); *G01R 19/0069* (2013.01); *G01R 19/16504* (2013.01); *F16C 2360/31* (2013.01)

(58) Field of Classification Search
CPC ................................. G01R 19/16504
See application file for complete search history.

(56) References Cited

U.S. PATENT DOCUMENTS

| | | | | |
|---|---|---|---|---|
| 4,163,389 A | * | 8/1979 | Suzuki | G01F 1/64 73/861.09 |
| 4,248,086 A | * | 2/1981 | Zizine | G01F 1/28 73/861.09 |

(Continued)

FOREIGN PATENT DOCUMENTS

| | | |
|---|---|---|
| DE | 102010025215 A1 | 12/2011 |
| DE | 102015225502 B3 | 6/2016 |
| JP | H09236124 A | 9/1997 |

OTHER PUBLICATIONS

German Search Report issued in corresponding German Patent Application No. 10 2016 211 615.0 dated Oct. 25, 2016.

*Primary Examiner* — Clayton E Laballe
*Assistant Examiner* — Jas Sanghera
(74) *Attorney, Agent, or Firm* — Davis & Bujold PLLC; Michael J. Bujold

(57) ABSTRACT

An arrangement with a first electrode (101), a second electrode (103), at least one measuring device (107) and at least one voltage source (109). The voltage source (109) is designed to apply a first electric voltage to the first electrode (101) and the measuring device (107) is designed to measure a second electric voltage at the second electrode (103). At least part of the first electrode (101) and at least part of the second electrode (103) are immersed in a flowing liquid.

14 Claims, 3 Drawing Sheets

(51) Int. Cl.
*G01R 19/00* (2006.01)
*G01R 19/165* (2006.01)
*F16C 41/00* (2006.01)
*F16C 19/52* (2006.01)

(56) References Cited

U.S. PATENT DOCUMENTS 5,807,526 A * 9/1998 Miljevic .............. B01D 53/32
                                                                           204/156
2005/0184734 A1 8/2005 Sosnowski et al.

* cited by examiner

NEUTRALIZATION OF CHARGED LUBRICANT

This application claims priority from German patent application serial no. 10 2016 211 615.0 filed Jun. 28, 2016.

FIELD OF THE INVENTION

The invention concerns an arrangement for neutralizing a charged lubricant.

BACKGROUND OF THE INVENTION

Electrical currents can cause damage in bearings. It is known that currents of the order of microamperes to amperes result in decarburization and sparking.

From the prior art oil filters are available, which are intended to prevent the lubricant to be filtered from becoming electrically charged. Such a filter is described, for example, in the document DE 10 2010 025 215 A1.

Recent research has shown that even small currents in the range of a few microamperes can be critical. It is suspected that such currents give rise to so-termed White Etching Cracks (WEC). However, the solutions known from the prior art are not suitable for eliminating currents in the microampere range.

SUMMARY OF THE INVENTION

The purpose of the present invention is to overcome the inadequacies and disadvantages inherent in the solutions known from the prior art. This should improve the robustness of bearings, in particular against the formation of White Etching Cracks.

This objective is achieved by an arrangement according to the claims.

The arrangement comprises a first electrode, a second electrode, at least one measuring device and at least one voltage source. Preferably, the arrangement is designed for use in a transmission, especially in a transmission of a wind turbine.

An electrode is understood to be an electron conductor which, in combination with a counter-electrode, interacts with a medium located between the two electrodes. The counter-electrode, with which the first electrode and the second electrode interact, is in this case preferably a ground conductor such as a transmission housing and/or at least one component electrically connected to the transmission housing.

The voltage source is designed to apply a first electric voltage to the first electrode. The first electric voltage is a potential difference between the first electrode and the counter-electrode.

The measuring device is designed to measure a second voltage applied to the second electrode. Analogously to the first voltage, the second voltage is a potential difference between the second electrode and the counter-electrode.

According to the invention, at least part of the first electrode and at least part of the second electrode are immersed in a flowing liquid. Accordingly, these parts of the first and second electrodes are in a common liquid flow.

The liquid flows around the parts of the first and second electrodes. Thereby, a charge transfer can take place between the liquid and the first electrode on the one hand, and the liquid and the second electrode on the other hand.

Thus, the size of the first electric voltage can influence the charging or electric potential of the liquid. By measuring the second electric voltage, the charging or electric potential of the liquid can be determined so as to, on the basis thereof, determine the value of the first electric voltage.

The liquid is preferably a lubricant. In particular it can be oil, such as transmission oil.

In a preferred further development, at least one component different from the first electrode and the second electrode gives rise to charging of the liquid, possibly when, in an also preferred further development, at least part of the component is in contact with the liquid so that the liquid flows around it as well as the first electrode and the second electrode. As described above, this charge can be neutralized by applying the first electric voltage and measuring the second electric voltage by means of the second electrode.

The component can in particular be a bearing, such as a roller bearing. It has been shown that roller bearings are not only damaged by current flows, but are themselves responsible for the generation of current flows. Such an effect is based on a mechanism of charge separation. The charge separation takes place in the roller bearing when a rolling body rolls over a bearing surface of the bearing.

Preferably, the arrangement is developed further with at least one control circuit. The first voltage is a controlled variable, the second voltage is a regulating variable, zero is a guide parameter, and the liquid flow is a control path of the control circuit. The control circuit comprises a regulator, which receives as an input a deviation, also called regulating deviation, of the controlled variable from the guide parameter. As a function of the regulating deviation, the regulator sets the controlled variable, i.e. the first voltage. By way of the first electrode, the first voltage influences the charging or electric potential of the liquid, i.e. that of the control path. Finally the charge or electric potential of the liquid flow is adopted as the regulating variable by the second electrode.

The structure of the control circuit described implies that liquid flows from the first electrode in the direction toward the second electrode. Thus, relative to the flow direction the second electrode is positioned after the first electrode. The flowing liquid flows past the first electrode before flowing past the second electrode.

In a preferred further development a disturbance variable of the control circuit is connected into the control path by the component. For this purpose, according to this further development the component or part thereof immersed in the liquid is positioned between the first electrode and the second electrode relative to the liquid flow. Thus, the liquid flows from the first electrode in the direction of the component or the part thereof immersed in the liquid, and from there onward toward the second electrode. Relative to the liquid flow, the component or the part thereof immersed in the liquid is positioned before the second electrode. In turn, relative to the liquid flow the first electrode is before the component or the part thereof immersed in the liquid. The first electrode is farther upstream than the component or the part thereof immersed in the liquid. In turn, the component or part thereof immersed in the liquid is farther upstream than the second electrode. Thus, the liquid flows past the first electrode before the component or the part thereof immersed in the liquid. Furthermore, the liquid flows past the component or the part thereof immersed in the liquid before reaching the second electrode.

The electric charging of the fluid brought about by the component is the disturbance variable of the control circuit. Since zero is specified as the guide parameter, the control circuit opposes the charging of the liquid by the component.

Alternatively, in an equally preferred further development, the liquid flows from the second electrode in the direction toward the first electrode. Thus, the positions of the first and second electrodes are interchanged compared with the arrangement described above. Correspondingly, the second electrode is before the first electrode in the liquid flow. The second electrode is farther upstream that the first electrode, and correspondingly the first electrode is farther downstream than the second electrode.

In this case no regulation, but a control is implemented. Accordingly, the first voltage is controlled as a function of the second voltage. The control system is designed such that the second voltage is neutralized by the first voltage, so that an electric potential difference of the liquid equal to zero is obtained.

With an arrangement of the second electrode upstream and the first electrode downstream, in an also preferred further development, the component is positioned before the second electrode. In this case the flowing liquid first passes the component or the part thereof immersed in the liquid, then the second electrode, and finally the first electrode. The component or the part thereof immersed in the liquid is farther upstream than the second and first electrodes. The first electrode is farther downstream than the component or the part thereof immersed in the liquid and the second electrode. Relative to the second electrode, the component or the part thereof immersed in the liquid is upstream and the first electrode is downstream.

The part of the first electrode immersed in the liquid and/or the part of the second electrode immersed in the liquid preferably have at least one point and preferably a plurality of point. Since the charge density is particularly high around a point, this improves the charge transfer between the first and second electrodes and the liquid.

In an also preferred further development, the first electrode and/or the second electrode have at least one wire made from an electrically conducting material. In particular, the first and/or the second electrode can have a plurality of wires. These are preferably woven into a mesh, they form a screen, or they are connected together in a grid.

The first and/or second electrode can even be developed further as a brush. A bristle of this brush forms the above-mentioned wire. In particular, all the bristles of the brush can be in the form of wires. Since each bristle of the brush ends in a point, a brush seems particularly suitable for transferring charges between the first or second electrodes and the liquid.

The bearing is preferably developed further in the form of at least one rolling element and at least one bearing surface over which the rolling element rolls when the bearing is rotating. The bearing surface is that of an outer ring, or preferably an inner ring of the bearing.

When the rolling element is rolling on the bearing surface, due to charge separation the liquid becomes electrically charged. To prevent this, the wire, which acts upon at least part of the liquid with an electric charge, is arranged so that at least part of the electrically charged portion of the liquid passes between the rolling element and the bearing surface. The effects of charging the liquid by the wire and of the charge separation due to the rolling of the rolling element on the bearing surface cancel out during this. Accordingly, liquid passes between the rolling element and the bearing surface whose charge is smaller or neutralized despite the charge separation effect taking place.

BRIEF DESCRIPTION OF THE DRAWINGS

Preferred example embodiments of the invention are illustrated hi the figures, in which matching indexes denote similar or functionally equivalent features. In detail, the figures show.

DETAILED DESCRIPTION OF THE PREFERRED EMBODIMENTS

Figure 1:
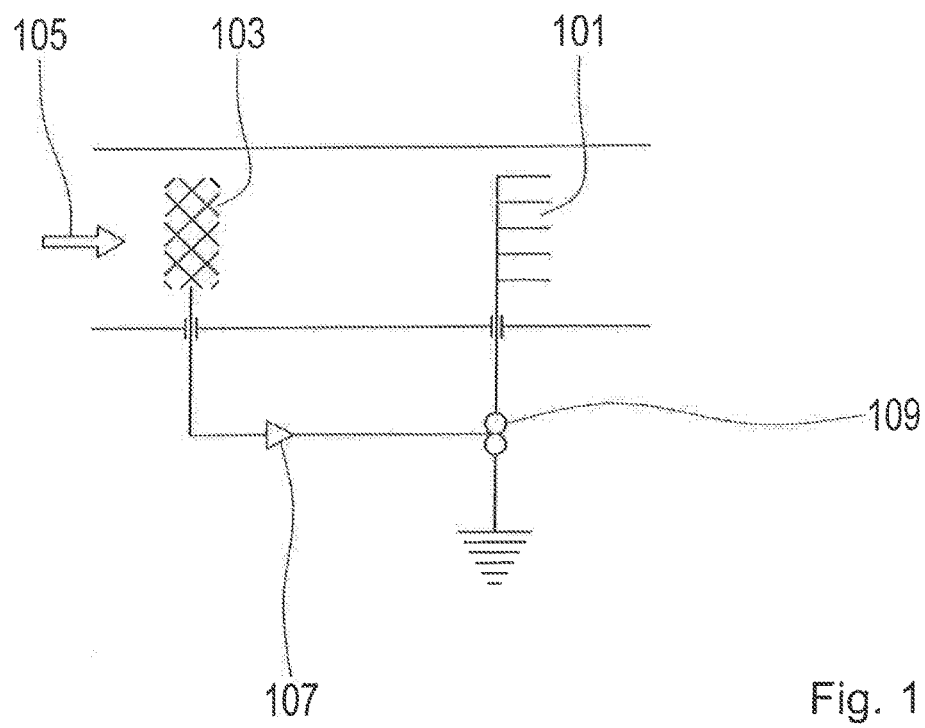
FIG. 1: Means for charge neutralization, in a first arrangement.

FIG. 1 shows a first electrode 101 and a second electrode 103. The first electrode 101 has a plurality of spikes. The second electrode 103 is in the form of a grid structure.

The two electrodes 101, 103 are arranged in a lubricant flow 105 in such manner that between the electrodes 101, 103 and the lubricant, a charge transfer can take place.

The first electrode 101 is electrically connected to a charge amplifier 107. This makes it possible to measure the charge of the liquid flowing past the second electrode 103.

Depending on the charge measured, the first electrode 101 has a voltage applied to it. For that purpose the first electrode 101 is electrically connected to a voltage generator 109.

Both the charge amplifier 107 and the voltage generator 109 are grounded.

Figure 2:
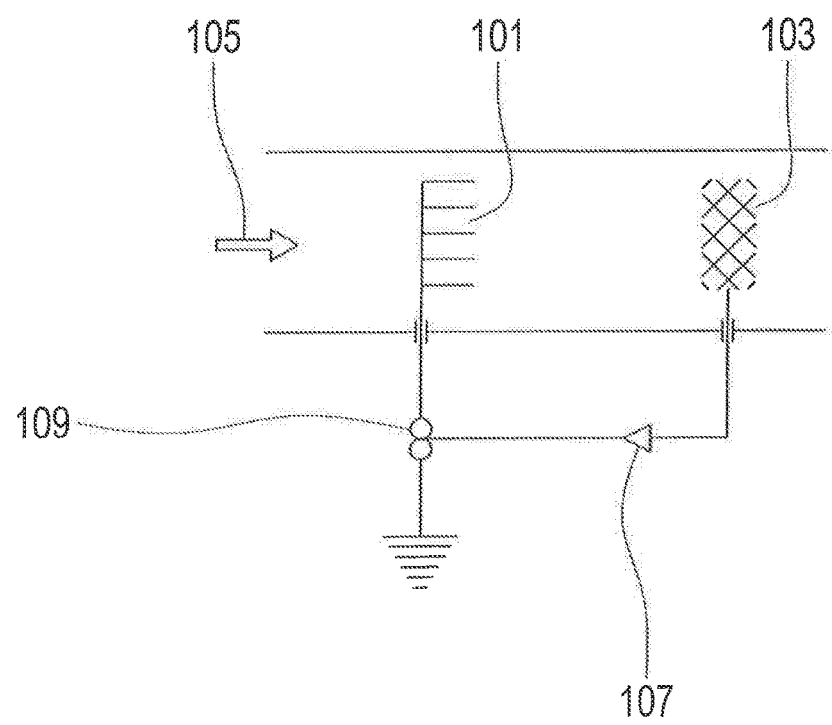
FIG. 2: Means for charge neutralization, in a second arrangement.

In FIG. 1 the first electrode 101 is positioned downstream and the second electrode 103 upstream. An inverse arrangement is shown in FIG. 2, in which the first electrode 101 is arranged upstream and the second electrode 103 downstream. In the arrangement according to FIG. 2 as well, the first electrode 101 is connected to the voltage generator 109 and the second electrode 103 to the charge amplifier 107.

Figure 3:
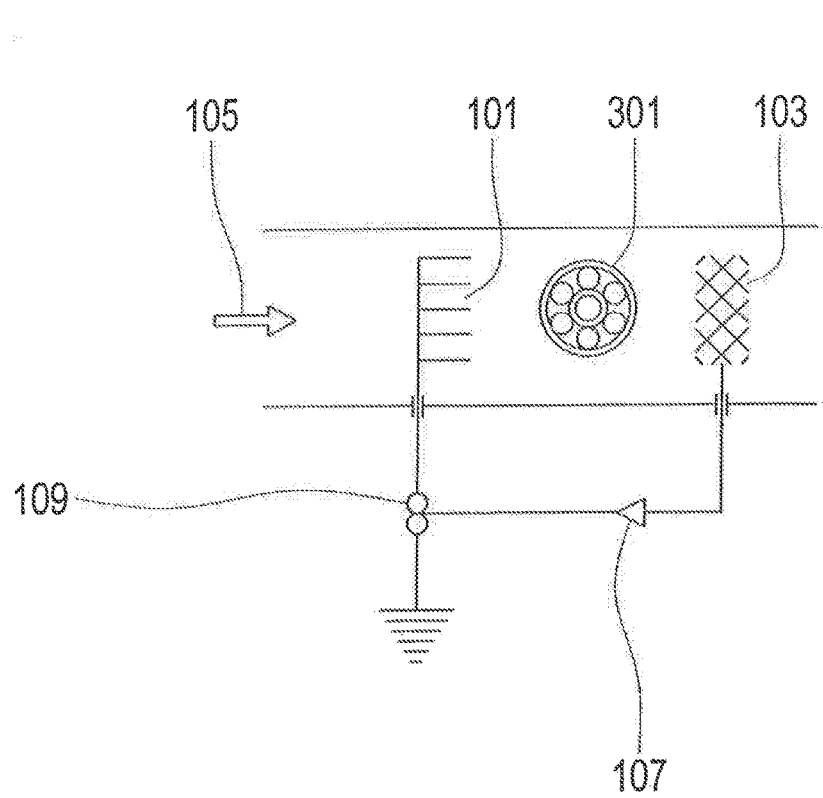
FIG. 3: The second arrangement with a roller bearing.

A possible application scenario is illustrated in FIG. 3. Here, besides the first electrode 101 and the second electrode 103, a roller bearing 301 is also in the lubricant flow. The roller bearing 301 is positioned between the first electrode 101 and the second electrode 103. When the lubricant flow 105 becomes electrically charged by the roller bearing 301, a charge transfer takes place at the second electrode 103, which can be measured in the form of a voltage.

In order to counteract the charging of the lubricant flow 105, a counter-voltage is applied to the first electrode 101. The lubricant flow that is oppositely charged by the first electrode 101 flows from the first electrode 101 to the roller bearing 301. There is still a charge separation taking place, but this now brings about a neutralization of the electric charge of the lubricant flow 105.

Figure 4:
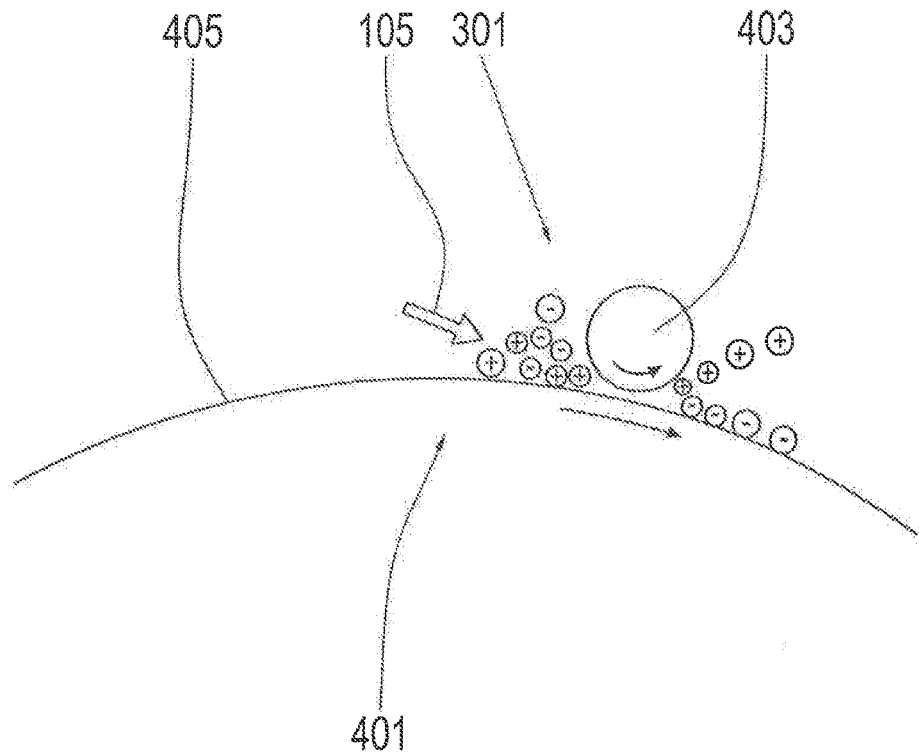
FIG. 4: Charge separation in a roller bearing.

The charge separation effect in the roller bearing 301 is shown more clearly in FIG. 4. This shows an inner ring 401 and a rolling element 403 of the bearing 301. When the rolling element 403 rolls over a bearing surface 405 of the inner ring 401, some of the lubricant flow 105, which is initially neutrally charged, makes its way between the rolling element 403 and the inner ring 401. During this a charge separation takes place.

Figure 5:
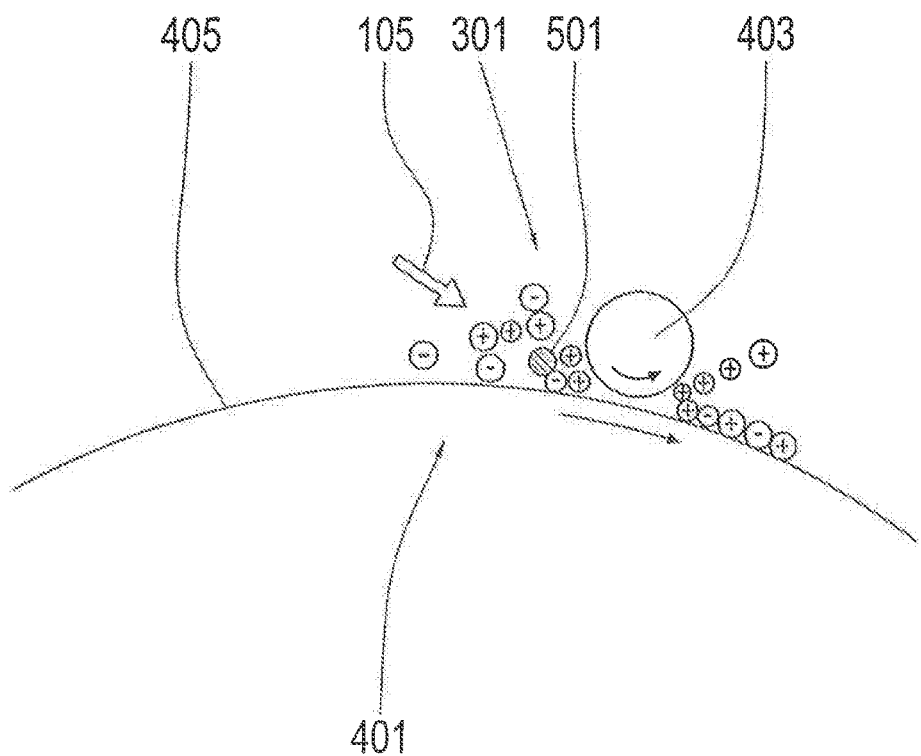
FIG. 5: The roller bearing with an electrode.

FIG. 5 additionally shows a wire 501 of the first electrode 101. Before the lubricant flow 105 makes its way between the rolling element 403 and the inner ring 401, it flows past the wire 501.

If now a voltage is applied to the wire, the lubricant flow is charged. This counteracts the charging due to the charge separation, i.e. the charge from the wire 201 and the charge due to charge separation have opposite signs.

INDEXES

101 First electrode
103 Second electrode

105 Lubricant flow
107 Charge amplifier
109 Voltage generator
301 Roller bearing
401 Inner ring
403 Rolling element
405 Bearing surface

The invention claimed is:

1. An arrangement comprising:
a first electrode;
a second electrode;
at least one measuring device;
at least one voltage source;
the voltage source being designed to apply a first electric voltage to the first electrode;
the measuring device being designed to measure a second electric voltage at the second electrode;
at least part of the first electrode and at least part of the second electrode being immersed in a flow of liquid; and
at least one component which causes the liquid to be electrically charged, the at least one component being a bearing.

2. The arrangement according to claim 1, wherein at least part of the component is immersed in the liquid.

3. The arrangement according to claim 2, wherein the part of the component immersed in the liquid is positioned in the flow of the liquid between the first electrode and the second electrode.

4. The arrangement according to claim 1, further comprising at least one control circuit with the first voltage as a controlled variable, the second voltage as a regulating variable, zero as a guide parameter and the flow of the liquid as a control path, and the flow of the liquid flows from the first electrode in a direction toward the second electrode.

5. The arrangement according to claim 1, wherein the flow of the liquid flows from the second electrode in a direction toward the first electrode, and the first voltage is controlled as a function of the second voltage.

6. The arrangement according to claim 5, wherein at least a part of the at least one component is immersed in the liquid and is positioned upstream of the second electrode.

7. The arrangement according to claim 1, wherein at least one of:
at least a part of the first electrode is immersed in the flow of liquid and has at least one spike; and
at least a part of the second electrode is immersed in the flow of liquid and has at least one spike.

8. The arrangement according to claim 1, wherein at least one of the first electrode and the second electrode has at least one wire consisting of an electrically conducting material.

9. The arrangement according to claim 8, wherein at least one of the first electrode and the second electrode is a brush, and the brush has the wire as a bristle.

10. The arrangement according to claim 1, wherein at least one roiling element of the bearing rolls on at least one bearing surface;
at least one of the first electrode and the second electrode has at least one wire consisting of an electrically conducting material, and the wire charges at least a portion of the liquid with an electric charge; and
the wire is arranged such that at least part of a portion of liquid that is electrically charged passes through between the rolling element and the bearing surface.

11. An arrangement for neutralizing an electrical charge of liquid in a liquid flow, the arrangement comprising:
a first electrode;
a second electrode;
at least one measuring device;
at least one voltage source;
the first electrode being electrically connected to the voltage source, and the voltage source applying a first electric voltage to the first electrode;
the second electrode being electrically connected to the measuring device, and the measuring device measuring a second electric voltage at the second electrode;
at least part of the first electrode being immersed in the liquid flow to transfer an electric charge from the first electrode to the liquid in the liquid flow, the, transferred electric charge corresponding to the first electric voltage, and at least part of the second electrode being immersed in the liquid flow such that an electric charge of the liquid in the liquid flow is applied to the second electrode, the second electric voltage corresponding to the applied electric charge; and
the first electric voltage applied by the voltage source to the first electrode being variable based on the second electric voltage at the second electrode measured by the measuring device such that the electrical charge of the liquid in the liquid flow through the arrangement is neutralized.

12. The arrangement according to claim 11, wherein the first electrode comprises at least one electrically conductive wire having a point and the second electrode comprises an electrically conductive mesh.

13. The arrangement according to claim 12, wherein a component is immersed in the liquid flow and facilitates further electrical charging of the liquid, and, with respect to the liquid flow, the first electrode is located upstream of the second electrode and the component is located between the first electrode and the second electrode, and the electrical charge applied to the second electrode comprises a combination of the electrical charge transferred to the liquid by the first electrode and the further electrical charging of the liquid facilitated by the component.

14. The arrangement according to claim 13, wherein the component is a bearing which comprises an inner ring and a rolling element, and the bearing is immersed in the liquid flow such that at least a portion of the liquid flow flows between the inner ring and the rolling element.

* * * * *